US012667493B2

(12) United States Patent
    Grübl

(10) Patent No.: US 12,667,493 B2
(45) Date of Patent: Jun. 30, 2026

(54) DEVICE FOR TREATING A TINNITUS AFFLICTION

(71) Applicant: Klaus Grübl, Braunau/Inn (AT)

(72) Inventor: Klaus Grübl, Braunau/Inn (AT)

( * ) Notice: Subject to any disclaimer, the term of this patent is extended or adjusted under 35 U.S.C. 154(b) by 711 days.

(21) Appl. No.: 18/008,942

(22) PCT Filed: Jun. 9, 2021

(86) PCT No.: PCT/EP2021/065486
§ 371 (c)(1),
(2) Date: Dec. 7, 2022

(87) PCT Pub. No.: WO2021/250104
PCT Pub. Date: Dec. 16, 2021

(65) Prior Publication Data
US 2026/0115048 A1     Apr. 30, 2026

(30) Foreign Application Priority Data

Jun. 9, 2020    (AT) .............................. A 50502/2020

(51) Int. Cl.
    *A61F 11/00*      (2022.01)
    *A61F 2/50*       (2006.01)
    *A61F 11/30*      (2022.01)
    *A61H 39/00*      (2006.01)
    *A61H 39/04*      (2006.01)
                (Continued)

(52) U.S. Cl.
    CPC ................ *A61F 11/30* (2022.01); *A61F 2/50* (2013.01); *A61F 2002/5021* (2013.01)

(58) Field of Classification Search
    CPC .. A61F 11/00; A61F 11/30; A61F 2/50; A61F 2002/5021; A61F 2002/5016; A61F 5/01; H04R 1/10; H04R 1/105; H04R 1/1091; H04R 25/00; H04R 25/02; H04R 25/65; H04R 25/75; G02C 11/00; G02C 11/06; A61H 39/04; A61H 39/00
See application file for complete search history.

(56) References Cited

U.S. PATENT DOCUMENTS 5,729,615 A * 3/1998 Yang .................... H04R 1/1066
                                              181/129
6,047,076 A * 4/2000 Yang .................... H04R 1/1066
                                              381/381
(Continued)

FOREIGN PATENT DOCUMENTS

CN          201608860 U   * 10/2010
CN          201608862 U   * 10/2010
                (Continued)

OTHER PUBLICATIONS

International Search Report for corresponding International Patent Application No. PCT/EP2021/065486 dated Aug. 19, 2021.
(Continued)

*Primary Examiner* — Edgardo San Martin
(74) *Attorney, Agent, or Firm* — Michael Fedrick; LOZA & LOZA, LLP

(57)                    ABSTRACT

The invention relates to a device for treating a tinnitus affliction and/or reducing stress, comprising an upper bracket (1), a lower bracket (2) and a pressure point body (3), wherein the upper and lower brackets are connected to each other by means of a plug-in connection (4).

10 Claims, 6 Drawing Sheets

(51) Int. Cl.
    *H04R 1/10*        (2026.01)
    *H04R 25/02*     (2006.01)

(56)             References Cited

U.S. PATENT DOCUMENTS

| | | | | |
|---|---|---|---|---|
| 6,377,697 | B1 * | 4/2002 | Cheng | H04R 1/083 |
| | | | | 381/381 |
| 6,427,018 | B1 * | 7/2002 | Keliiliki | H04R 1/1066 |
| | | | | 381/381 |
| 6,580,800 | B1 * | 6/2003 | Yamasaki | H04R 1/105 |
| | | | | 381/381 |
| 6,584,208 | B2 * | 6/2003 | Cheng | H04R 1/083 |
| | | | | 381/381 |
| 6,819,772 | B2 * | 11/2004 | Amae | H04R 1/105 |
| | | | | 381/374 |
| 6,914,997 | B2 * | 7/2005 | MacDonald | H04R 1/10 |
| | | | | 379/426 |
| 8,230,965 | B1 * | 7/2012 | Lederman | A61F 11/30 |
| | | | | 181/129 |
| 9,241,868 | B2 * | 1/2016 | Wardle | A61H 39/04 |
| 11,606,654 | B2 * | 3/2023 | Grübl | A61F 11/14 |
| 2017/0303031 | A1 | 10/2017 | Barry | |
| 2019/0117508 | A1 * | 4/2019 | Kimura | H04R 1/105 |
| 2019/0261077 | A1 | 8/2019 | Dominijanni et al. | |
| 2024/0179477 | A1 * | 5/2024 | Jinde | H04R 25/606 |

FOREIGN PATENT DOCUMENTS

| | | | | | |
|---|---|---|---|---|---|
| CN | 205598091 | U | | 9/2016 | |
| CN | 106233748 | A | | 12/2016 | |
| CN | 206743497 | U | | 12/2017 | |
| CN | 120022532 | A | * | 5/2025 | A61F 11/00 |
| DE | 2910315 | A1 | | 9/1980 | |
| DE | 10139865 | | | 4/2003 | |
| DE | 102011101662 | A1 | * | 11/2012 | A61N 1/36014 |
| GB | 2450931 | A | | 1/2009 | |
| JP | 2009095627 | | | 5/2009 | |
| JP | 3164048 | U | * | 11/2010 | A61F 11/30 |
| JP | 5856346 | B1 | * | 2/2016 | |
| JP | 6389576 | B1 | * | 9/2018 | H04R 25/607 |
| JP | 6463546 | B1 | * | 2/2019 | A61F 11/30 |
| JP | 2020039663 | | | 3/2020 | |
| JP | 2021121857 | A | * | 8/2021 | |
| JP | 7018231 | B1 | * | 2/2022 | |
| JP | 2024076509 | A | * | 6/2024 | H04R 25/604 |
| WO | 2015164889 | A1 | | 10/2015 | |
| WO | 2019158674 | | | 8/2019 | |
| WO | WO-2024084026 | A1 | * | 4/2024 | A61F 11/00 |
| WO | WO-2024105093 | A1 | * | 5/2024 | A61H 39/04 |

OTHER PUBLICATIONS

Written Opinion for corresponding International Patent Application No. PCT/EP2021/065486 dated Aug. 19, 2021.
Office Action for Austrian Patent Application No. 50502/2020 dated Apr. 20, 2021, 6 pgs.
Search Report for Austrian Patent Application No. 50502/2020 dated Apr. 20, 2021, 1 pg.
International Search Report for corresponding International Patent Application No. PCT/EP2021/065486, dated Sep. 2, 2021.
Second Office Action for Chinese Patent Application No. 202110405854.8 dated Jan. 26, 2026, 16 pgs.

\* cited by examiner

DEVICE FOR TREATING A TINNITUS AFFLICTION

CROSS-REFERENCE TO RELATED APPLICATIONS

This application is the U.S. national stage of International Patent Application No. PCT/EP2021/065486, filed on Jun. 9, 2021 and entitled DEVICE FOR TREATING A TINNITUS AFFLICTION, which claims the benefit of priority under 35 U.S.C. § 119 from Austrian Patent Application No. A 50502/2020, filed on Jun. 9, 2020. The disclosures of the foregoing applications are incorporated herein by reference in their entirety.

FIELD OF THE INVENTION

The present invention relates a device for treating a tinnitus affliction and/or reducing stress.

BACKGROUND ART

Tinnitus is an auditory perception that is perceived on one or both sides in addition to the sound acting on the ear. This perception is based on a disruption of the hearing function. The type of apparent noise is very diverse: the auditory impressions are described as buzzing or whistling, hissing, rustling, clicking or knocking.

Tinnitus impairs quality of life. Previous treatment methods (including various forms of acoustic stimulation, approaches involving behavioral therapy, combined therapy approaches involving acoustic stimulation and elements of behavioral therapy (e.g., tinnitus retraining therapy), drug therapy methods, physiotherapy, magnetic and electrical brain stimulation methods) do not always work, or do not work well enough. For most of the therapies offered, there is no evidence of activity through sufficiently large placebo-controlled studies.

The prior art describes, for example, an ear device which is intended to compensate for rapid pressure changes due to rapid changes in altitude in aircraft in or-der to avoid ear pain. For example, GB2450931 describes earmuffs in which pressure can be regulated using an air pump.

In hearing protectors which are worn as sound protectors, a heat build-up occurs after prolonged use, which can lead to excessive perspiration. In order to enable an air exchange, a ventilation opening is provided on the capsule of the hearing protector. By changing the volume of the capsule interior, the air exchange is thus made possible (DE2910315).

CN205598091 (U) describes a device comprising eyeglasses, a Bluetooth headset and headphones. By means of this device, for example, environmental and other sounds or music for treating tinnitus can be played using software.

WO2015164889 describes a headphone that, in use, is locatable within or near an ear canal of a user, and an ear loop to secure the earphone to the ear of the user. The ear loop comprises an inflatable bladder to better secure the earphone, in use, to the ear of the user. US20170303031 describes headphones comprising an inflatable mounting system to better secure the housing of the headphone to the human ear. CN206743497 describes a headphone with an inflatable balloon, but which is attached in the inner ear.

WO2019158674 describes a device for treating a tinnitus affliction, comprising a body which is dimensioned in such a way that it can be secured to or in close proximity to the auricle, characterized in that said body has at least one punctual balloon whereby the position of the auricle is changed. Preferably, the punctual balloon is attached on a temple. However, this device has the disadvantage that it can only be adapted very inaccurately and with difficulty to the requirements of the respective wearers.

Tinnitus may well be curable. In particular in acute tinnitus, the prospects of healing are good. However, there are no exact numbers of how many people afflicted with tinnitus are cured in what form. A tinnitus patient may be considered healed when his/her ear noise has disappeared. Therefore, there is still a need for targeted, permanent and successful treatment of tinnitus. Therefore, the object of the present invention is to provide a device and the use thereof, in which the pressure point body is easy to position, can be adapted by the user to his/her individual needs, and can be worn comfortably.

SUMMARY OF INVENTION

The object is achieved by the independent claims. The present invention thus comprises a novel device for treating tinnitus and/or reducing stress, wherein said device changes the position of the auricle and thus changes the angle of incidence of sound. This change in the outer ear alleviates the tinnitus affliction and/or cures it entirely.

In particular, the present invention relates to a device for treating a tinnitus affliction and/or reducing stress, comprising an ear bracket consisting of an upper (1) and a lower bracket (2), and a pressure point body (3). The device is dimensioned in such a way that it can be worn behind the auricle (exterior ear).

The pressure point body (3) can be made in different sizes and shapes. The position of the pressure point body on the bracket can be individually adjusted to the respective wearer. Any necessary readjustments of the position of the pressure point body can be carried out independently by the wearer.

One embodiment comprises the device as described herein, wherein the device consists of an upper and a lower bracket connected by means of a plug-in connection (4). This connection allows the position of the upper and lower brackets to be changed with respect to each other. This ensures that the device can be opened (FIG. 4) to allow easier behind ear attachment.

By means of this movable embodiment it can be achieved that the device can be held on the ear of the user in the position in which the pressure point body can be positioned at the desired position behind the outer ear of the user. The device can be held in this position without a clamping force or the like permanently having to act on the ear of the user. As a result, wearing the device according to the invention becomes more comfortable compared to the solutions according to the prior art. Furthermore, the device according to the invention can be designed to have a relatively small volume, since it is secured directly behind an ear of the user. The attachment to the user's ear can also be carried out easily and can be carried out with one hand.

Likewise, the optimum pressure and wearing comfort for the wearer can thereby be set individually. In one embodiment, this connection is a splint connection. However, any other suitable means of connection may be used.

One embodiment comprises the device as described herein, wherein the lower bracket has a cut (5) (FIG. 1). This cut may be formed as an opening, notch, slot, gap, or the like. The pressure point body is secured in this cut. The position of the pressure point body can then be changed variably along the cut, so that the pressure point body can be adapted individually to the requirements of the wearer.

The pressure point body is secured in this cut with suitable securing means in such a way that the position along this cut is variable and can be changed. For example, the pressure point body can completely enclose a part of the bracket or enclose both parts of the bracket. The pressure point body can be secured in the slot, for example, by means of a clamping connection.

Since these devices are to be worn by the patients over a relatively long period of time, pleasant wearing comfort and individual adaptation of the position of the pressure point body are indispensable. On the one hand, in order to ensure the healing progress and, on the other hand, in order to ensure the necessary wearing period by the patient over several weeks or even months due to the increased wearing comfort.

One embodiment comprises the device as described herein, wherein the upper bracket has a recess (FIG. 3). Inlays can be introduced into this recess. These inlays also improve the wearing comfort for the patient.

One embodiment comprises the device as described herein, wherein the lower bracket (2) has a jacket (8) (FIG. 10). This jacket can be made of any material that assists in comfortably wearing the device.

One embodiment comprises the device as described herein, wherein the lower bracket (2) has a certain flexibility. This means that the lower bracket can, for example, additionally exert a pressure on the ear in addition to the pressure point body. As a result, for example, the effect of alleviating the tinnitus affliction can be enhanced.

The present invention further comprises the use of the device according to the invention for treating a tinnitus affliction.

One embodiment comprises the use of the device according to the invention for treating a tinnitus affliction, wherein the position of the auricle (outer ear) is changed by the device, in particular by the pressure point body.

The device is particularly suitable for treating a tinnitus affliction, wherein the angle of incidence of sound at the outer ear is changed by the device, in particular by the pressure point body.

Pressure is exerted on the auricle (outer ear) by means of the device according to the invention, in particular by the pressure point body. This pressure allows the middle ear to be deformed and thus the sound to be refracted differently, as a result of which disturbing noises are alleviated and ultimately a relief and consequently even a healing of a tinnitus affliction is made possible.

Stress refers, on the one hand, to psychological and physical reactions in living creatures caused by specific external stimuli (stressors) which enable special requirements to be met and, on the other hand, to the physical and mental stress created thereby. Stress is understood as meaning the strain and the associated effect of the burden of humans due to internal and external stimuli or burden. This burden can be both artificially and naturally, both biotically and abiotically, have an effect both on the body and on the psyche of humans and can ultimately be perceived as positive or negative, or have a positive or negative effect. Coping with strain depends on personal attributes as well as aspects of health and cognitive abilities of each person.

Stress has an effect on psyche as well as on physical well-being. Mild and severe diseases may occur, such as for example forgetfulness and concentration disorders, sleep disorders, reduced physical capacity and creativity, nervous restless behavior, fast talking and eating, restlessness, decision-making difficulties, communication difficulties, multitasking, activism, lack of planning, confusion, difficulties in time management, "not getting done", taking work home, inefficiency, inability to relax, not taking vacation, less time off, neglecting relationships and family, lack of physical activity, uncontrolled eating and smoking, increased alcohol consumption, excessive coffee consumption, taking pain killers, tranquilizers, sleeping aids and stimulants, permanent worrying and "thinking about the future", feeling rushed and under pressure, going around in circles and pondering, nocturnal thinking of work-related issues, "black out", inner void, anxiety, exhaustion, inner restlessness and tension, irritability and aggression, mood changes, dissatisfaction and depressed mood.

The vegetative nervous system consists of two components which are active simultaneously. One part, the so-called sympathicus, provides tension, the other part, the parasympathicus provides relaxation. Stress leads to tension and, in the case of permanent tension, the vegetative nervous system hereby tips over into a mode of overactivation of the sympathicus while the parasympathicus is responsible for the reduction of the stress in the human body. This lower area of the bracket (FIGS. 2, 8) rests on the ear at a location where the vegetative nervous system, more precisely the parasympathicus, is also stimulated. Due to this stimulation, a reduction in stress could be observed in wearers of the bracket according to the invention.

DESCRIPTION OF EMBODIMENTS

Figure 1:
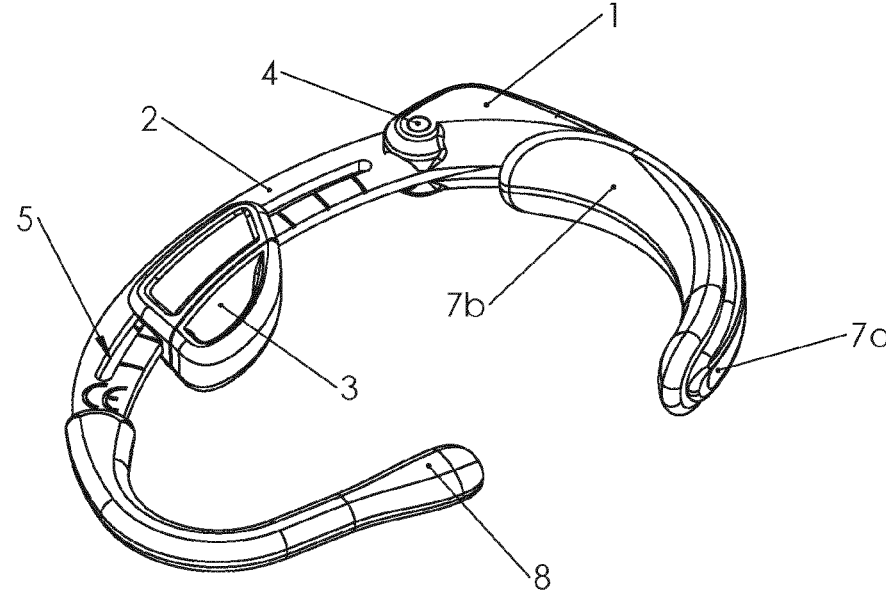
FIG. 1 shows the device in the form of a bracket consisting of a lower and upper bracket, and a pressure point body.

The effects of tinnitus strongly depend on the subjective perception and assessment of ear noises. These ear noises can occur on one side or on both sides.

Tinnitus aurium means "the ringing of the ears". Medically, tinnitus is defined as an acoustic perception that arises without a corresponding acoustic stimulus from outside the body and does not contain any information.

In principle, two forms are distinguished. In objective tinnitus, there is an intrinsic sound source in the ear or near the ear, the sound emissions of which are perceived. This is to say, the noises often emanating from the blood vessels or the muscle actually exist and thus others can hear them also, albeit usually only with the stethoscope or other medical devices.

However, subjective tinnitus is much more common. In this case, persons affected perceive sounds and noises which cannot be attributed to a physical source of sound and therefore cannot be heard by other people. However, this in no way means that the patients only imagine the buzzing, humming, whistling, ringing, rustling or knocking. Rather, subjective tinnitus is due to erroneous information formation or processing in the auditory system, extending from the ear through the auditory nerve to the auditory centers in the brain.

In the case of many persons affected, however, it cannot be determined definitely what the ear noises are attributed to. This is referred to as idiopathic tinnitus.

Surprisingly, it has now been found that by changing the position of the outer ear relative to the remaining ear, the sound is changed, that is to say the sound is refracted in comparison to the "normal incidence". This results in a different point of impact at the tympanic membrane. As a result, the hammer (grip) of the first auditory bone is moved differently and transmits changed pressure signals to the next auditory bone or then further to the cochlea. In the cochlea, the sensory hairs stored in a liquid are set in motion differently. This leads to a changed conversion of the electrical signals into the brain and to a change of the synapses in terms of learning—the previous sounds are no longer heard and thus "forgotten" in the long term.

As a result of changes in the angle of incidence of sound, the ear noises (tinnitus) perceived as "disturbing" are no longer perceived, since the sound impinges on other points of impact on the tympanic membrane.

Different refractions (change of path length) result in sound having different frequencies. Frequency change by distance change between observer (tympanic membrane) and sound source (Doppler effect). The sound path in the ear between the outer ear and the tympanic membrane changes. Therefore, the previous "old" frequencies, which were perceived as disturbing, are no longer perceived since they have changed "in frequency" and are no longer perceived in the brain. This will mainly occur at high frequencies.

With the device according to the invention, the angle of incidence of sound is changed in such a way that the persons affected no longer hear the previously learned disturbing sounds. The device according to the invention therefore comprises a bracket with a pressure point body which is dimensioned in such a way that it can be secured to the auricle, wherein the position of the auricle is changed by the pressure point body. By changing the position of the outer ear through this pressure point body, the angle of incidence of sound into the ear is changed, as a result of which the patients will no longer hear the previous sounds and even forget to hear them long-term.

In particular, it is advantageous to exert pressure to the outer ear by the pressure point body. This pressure can lead to the position of the outer ear being changed in such a way that the angle of incidence of the sound is likewise changed and thus disturbing tinnitus sounds are no longer heard. The perception of noises, which are not caused by the acoustic signals from the environment, is reduced or entirely eliminated with the device according to the invention.

Figure 9:
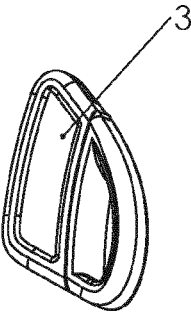
FIG. 9 shows pressure point bodies of different designs.
Figure 9:
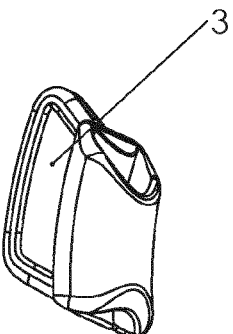
Figure 10:
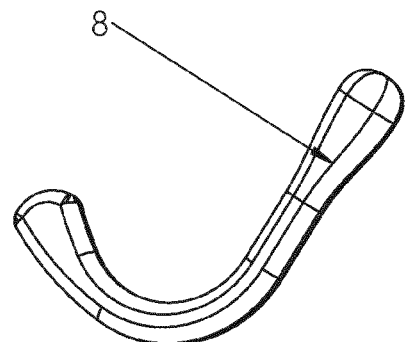
FIG. 10 shows a jacket for the lower part of the lower bracket.

The pressure point body is attached on the device according to the invention in an individually changeable manner, which device can be secured to or behind the auricle. The pressure point body can have different shapes and sizes. Exemplary pressure point bodies are depicted in FIG. 9.

An embodiment according to the invention is a bracket consisting of an upper and a lower bracket part, which are connected to each other by means of a plug-in connection and can be opened, and which can be worn behind the ear.

The pressure point body can be produced from different materials. In principle, any material can be used which is suitable to form a corresponding shaped body and is comfortable to wear. For example, the pressure point body can be made of plastic, fabric, felt, foam, gel, rubber, elastic adhesive strips or similar materials. The pressure point body can be made of a foamed material, an elastic deformable material, or a plastic material, for example polypropylene.

The upper and the lower bracket may be made of stable materials.

Particularly suitable are, for example, stainless steel, titanium, spring steel, other metals and metallic alloys, plastics, and the like.

Figure 3:
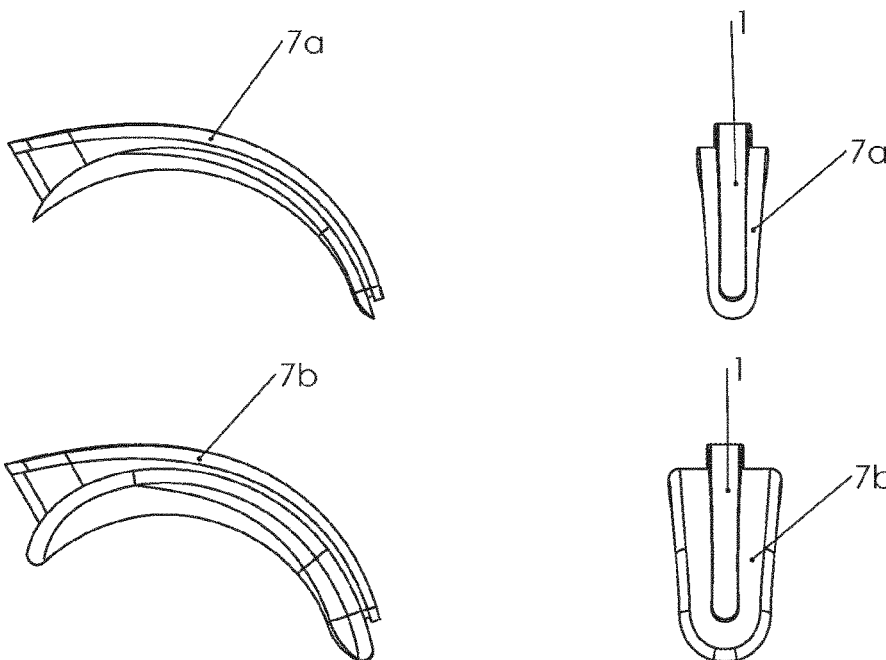
FIG. 3 shows a side and front view of the upper bracket with inlays.

In order to increase the wearing comfort for the patients, inlays can be introduced into the upper bracket (FIG. 3), for example. These inlays consist of a suitable material such as for example silicones, rubber, plastic, fabric, felt, foam, gel, rubber or similar materials.

The lower bracket may be partially jacketed. Such a jacket (8) also serves for wearing comfort. The jacket can in turn be made from a suitable material, in particular, for example, rubber.

EXEMPLARY EMBODIMENTS

The following embodiments illustrate the present invention without limiting it in its scope.

One embodiment is depicted in FIG. 1. It consists of an upper bracket (1) and a lower bracket (2), which are flexibly connected to each other by means of a plug-in connection (4). A pressure point body (3) is secured on the lower bracket (2). The pressure point body is movably mounted on the lower bracket. That is to say, the pressure point body can be displaced along the upper part of the lower bracket (2). Inlays are optionally attached to the upper bracket (1). The lower bracket is jacketed in the lower part.

Figure 2:
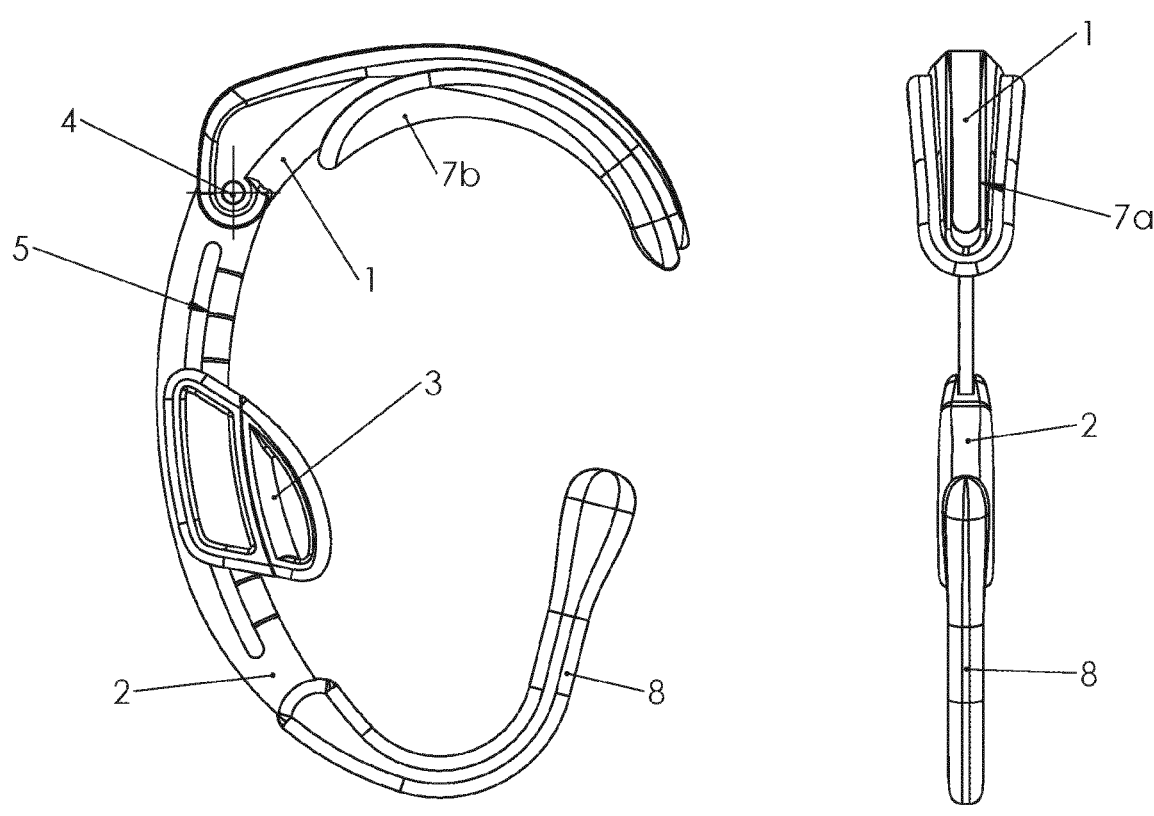
FIG. 2 shows a side and front view of the device consisting of a lower and upper bracket, and a pressure point body.
Figure 4:
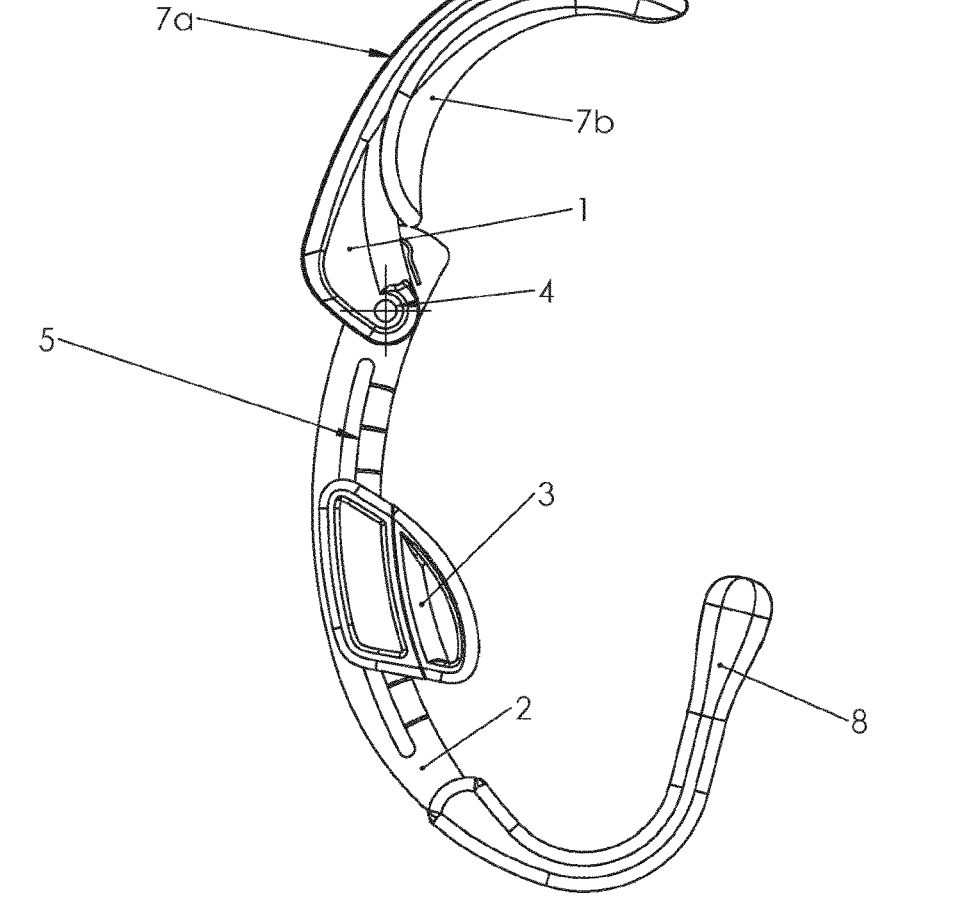
FIG. 4 shows a side view of the opened device.
Figure 5:
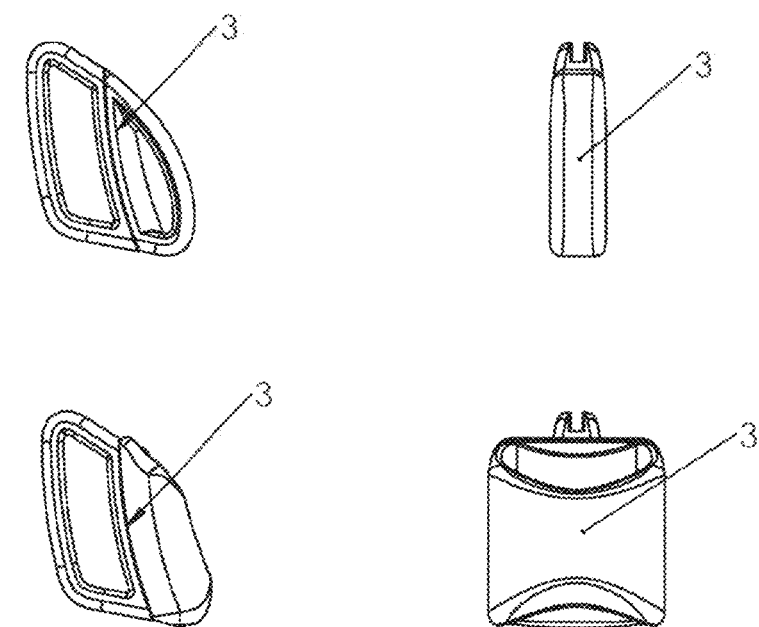
FIG. 5 shows a side and front view of pressure point bodies of different designs.
Figure 6:
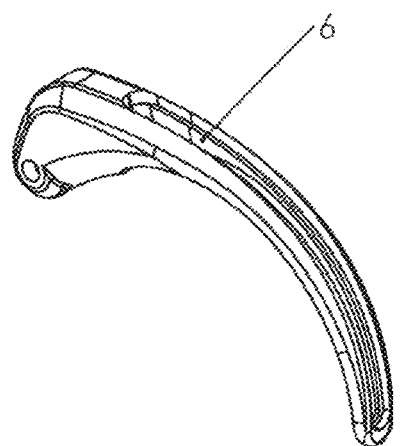
FIG. 6 shows the upper bracket of the device.
Figure 7:
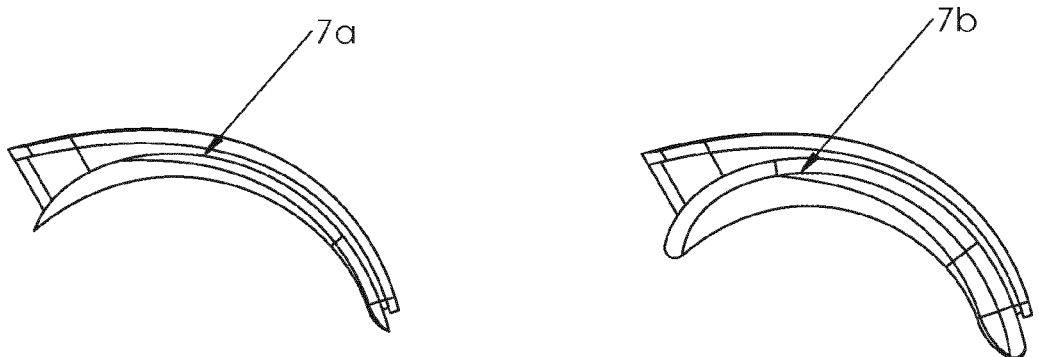
FIG. 7 shows different inlays.
Figure 8:
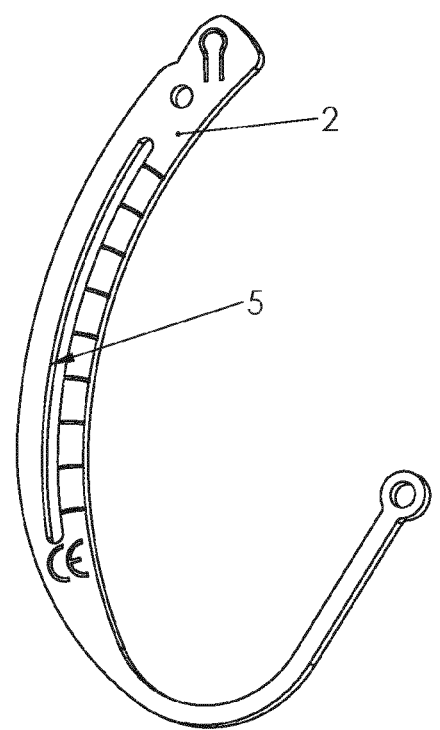
FIG. 8 shows the lower bracket with slot.

FIG. 2 shows a schematic depiction of the device in closed form. FIG. 4 shows a schematic depiction of the device in open form which facilitates the attachment of the device behind the ear.

In a first application observation with 36 users who used the bracket according to the invention for at least 6 weeks, it was analyzed how the stress level of the users had changed. Here, the users reported daily their subjectively perceived stress on a scale of 0 to 10. A linear trend analysis was calculated for each individual user.

Figure 11:
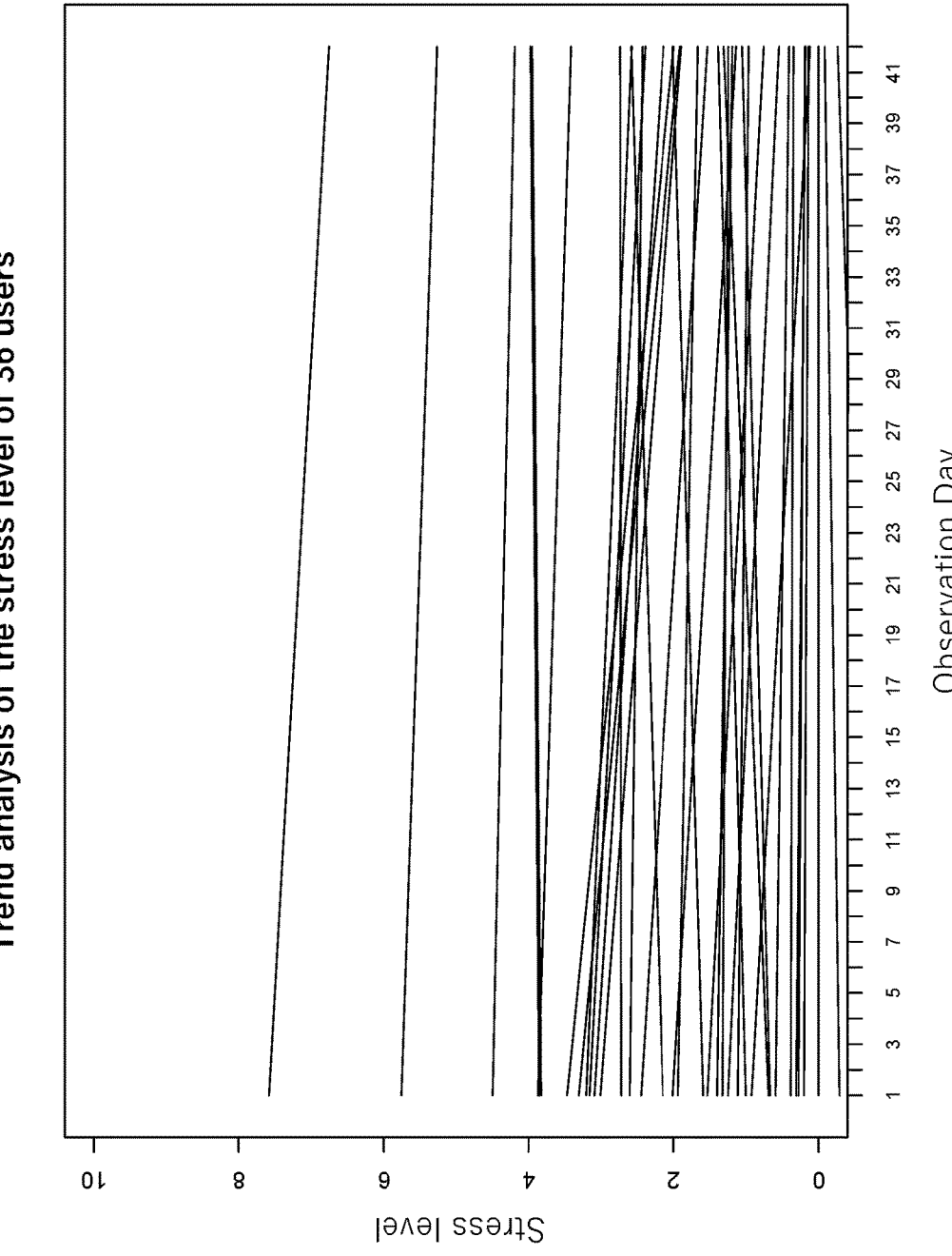
FIG. 11 shows the trend analysis of the stress level of 36 users.

For 19 of the 36 users (52.7%), the stress level has been reduced in a statistically significant manner while using the bracket according to the invention (see FIG. 11).

The invention claimed is:

1. A device for treating a tinnitus affliction and/or reducing stress, comprising an upper bracket, a lower bracket and a pressure point body, wherein characterized in that the upper and lower brackets are connected to each other by means of a plug connection, wherein the lower bracket has a horizontal cut in which the pressure point body is attached, and wherein the pressure point body exerts pressure on the outer ear and changes the position of the outer ear.

2. The device according to claim 1, characterized in that the plug connection is a splint connection.

3. The device according to claim 1, characterized in that the pressure point body is secured in the horizontal cut.

4. The device according to claim 3, characterized in that the pressure point body is freely movable along the horizontal cut.

5. The device according to claim 1, characterized in that the upper bracket has a recess.

6. The device according to claim 5, characterized in that one or two inlays are attached in the recess.

7. The device according to claim 1, characterized in that the lower bracket has a jacket.

8. The device according to claim 7, characterized in that the jacket consists of a soft material.

9. The device according to claim 1, characterized in that the lower bracket is movable.

10. The device according to claim 8, characterized in that the jacket consists of rubber.

\* \* \* \* \*